United States Patent [19]

Adair

[11] Patent Number: 5,498,230
[45] Date of Patent: Mar. 12, 1996

[54] STERILE CONNECTOR AND VIDEO CAMERA COVER FOR STERILE ENDOSCOPE

[76] Inventor: Edwin L. Adair, 317 Paragon Way, Castle Pines Village, Colo. 80104

[21] Appl. No.: 317,199

[22] Filed: Oct. 3, 1994

[51] Int. Cl.[6] ............................................. A61B 1/04
[52] U.S. Cl. ........................... 600/112; 600/124; 600/122
[58] Field of Search ................................... 600/122–124, 600/121, 112

[56] References Cited

U.S. PATENT DOCUMENTS

| | | | |
|---|---|---|---|
| 4,590,923 | 5/1986 | Watanabe | 600/122 |
| 5,311,859 | 5/1994 | Monroe et al. | 600/112 |

*Primary Examiner*—Richard J. Apley
*Assistant Examiner*—John P. Leubecker
*Attorney, Agent, or Firm*—Fields, Lewis & Rost

[57] ABSTRACT

A sterile connector and video camera cover is provided including a connector assembly for connecting a sterile endoscope to an unsterile surgical camera and a light fiber cable. The camera cover is extendable over the camera, its trailing cables and the light fiber cable. The connector assembly includes a coupling and a light fiber connection. The coupling includes a transverse window providing a sterile barrier and an optically clear path for light to pass through. The light source connection is mounted on the connector assembly enabling a light fiber cable to be optically coupled with the fiber optics of an endoscope. The coupling and the light source connector have a common exterior surface and are housed within the connector assembly. An adapter is provided enabling connection of the connector assembly with endoscopes having either threaded connections or compression-type fittings. A slot is provided on the connector assembly to engage a ball detent of the camera to ensure the camera remains rigidly fixed during use. A sterile disposable wand is attachable to the end of the connector assembly receiving the endoscope. This wand aides in connection of the camera to the coupling and is removed so that the endoscope can be attached to the coupling.

11 Claims, 3 Drawing Sheets

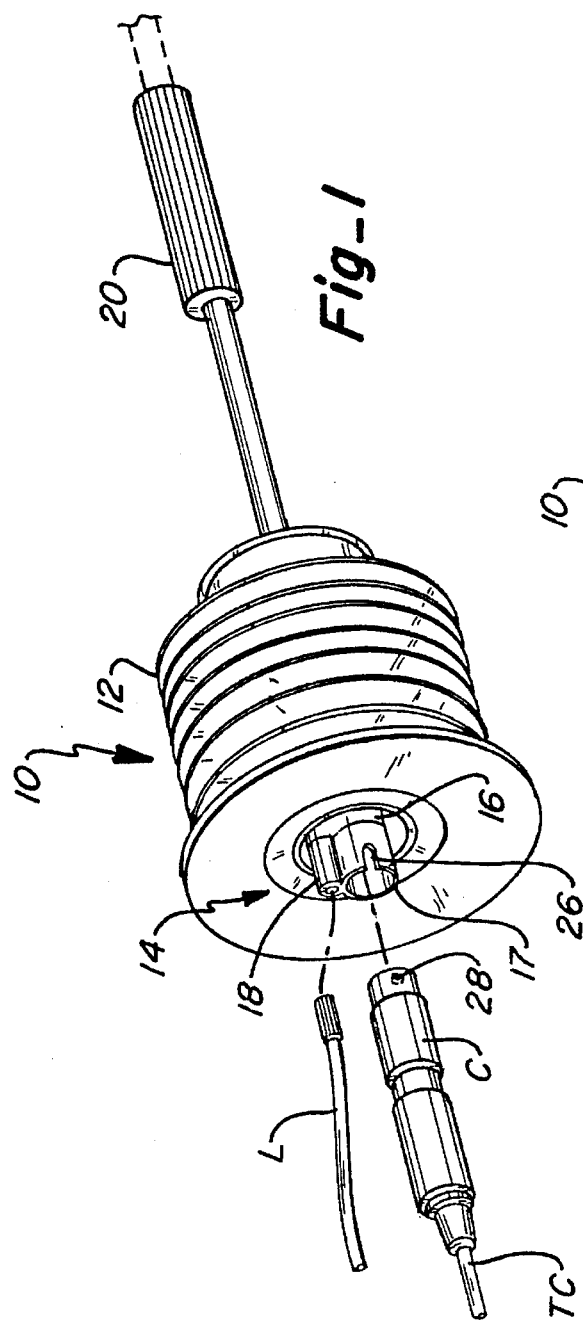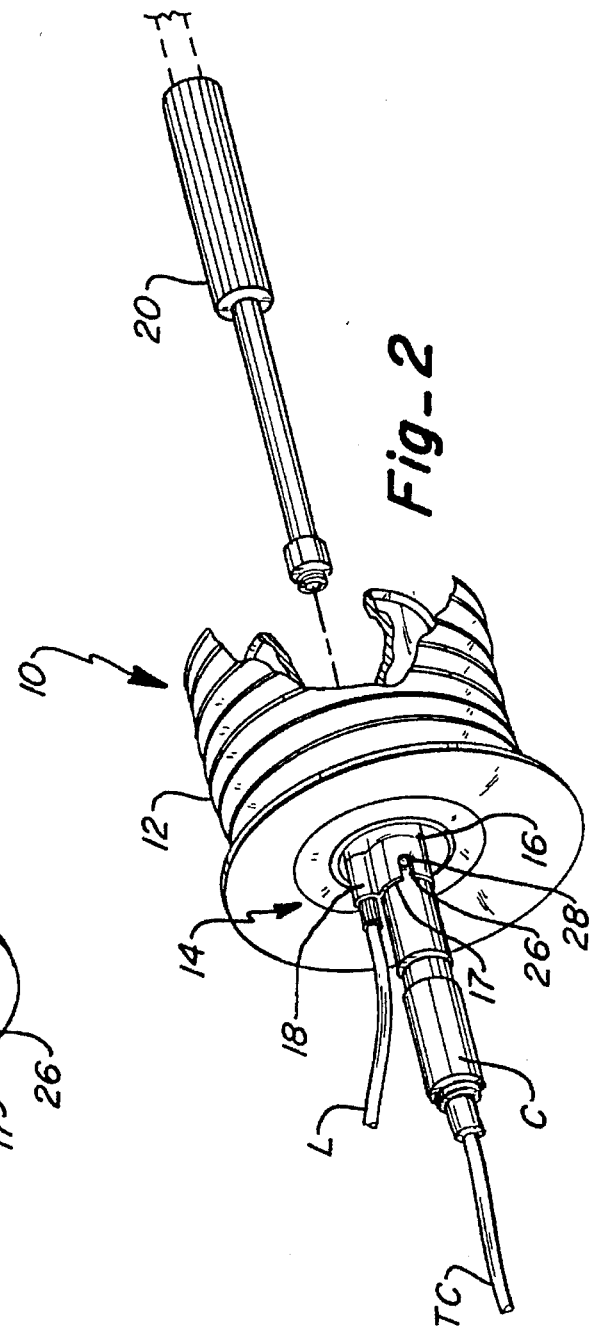

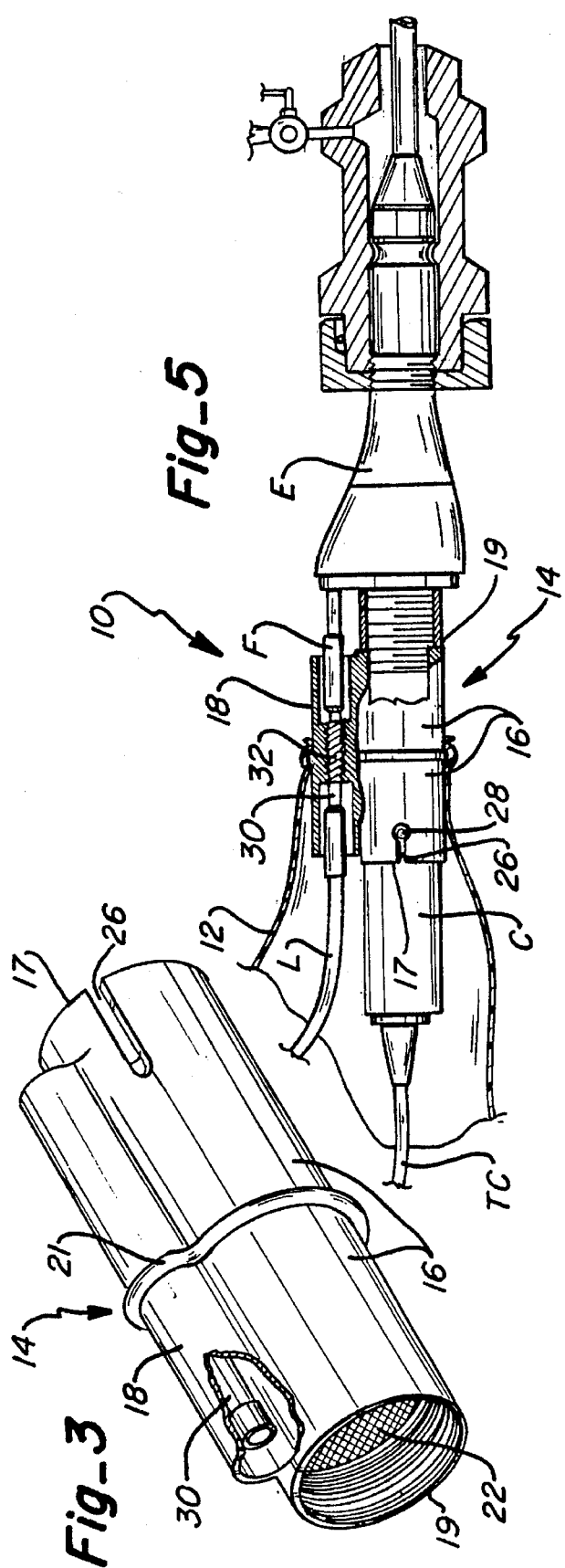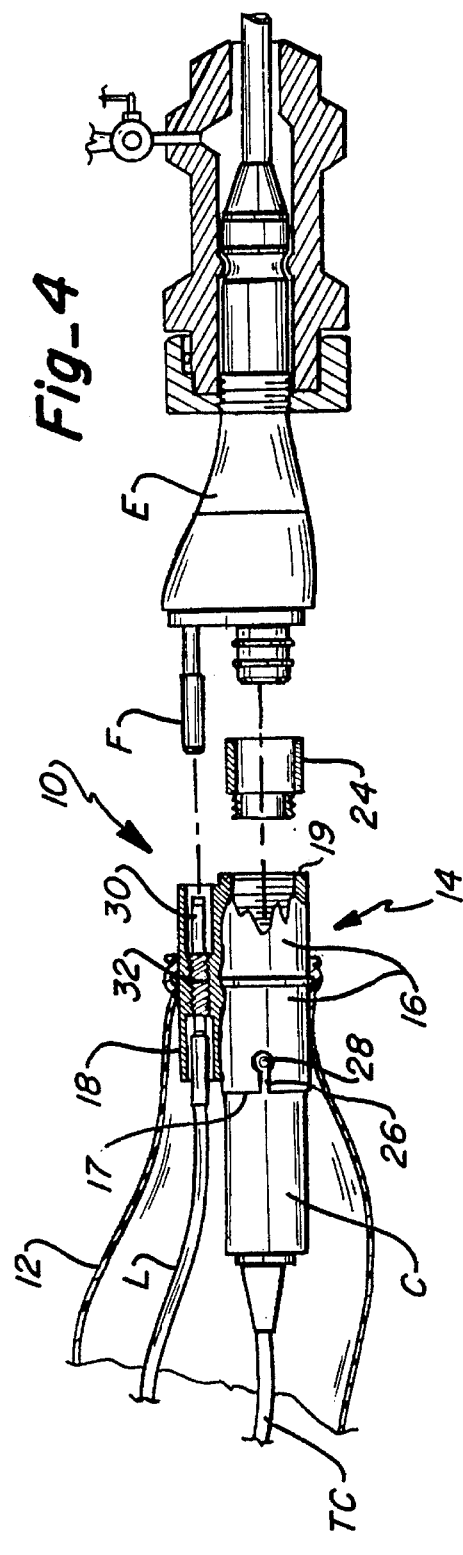

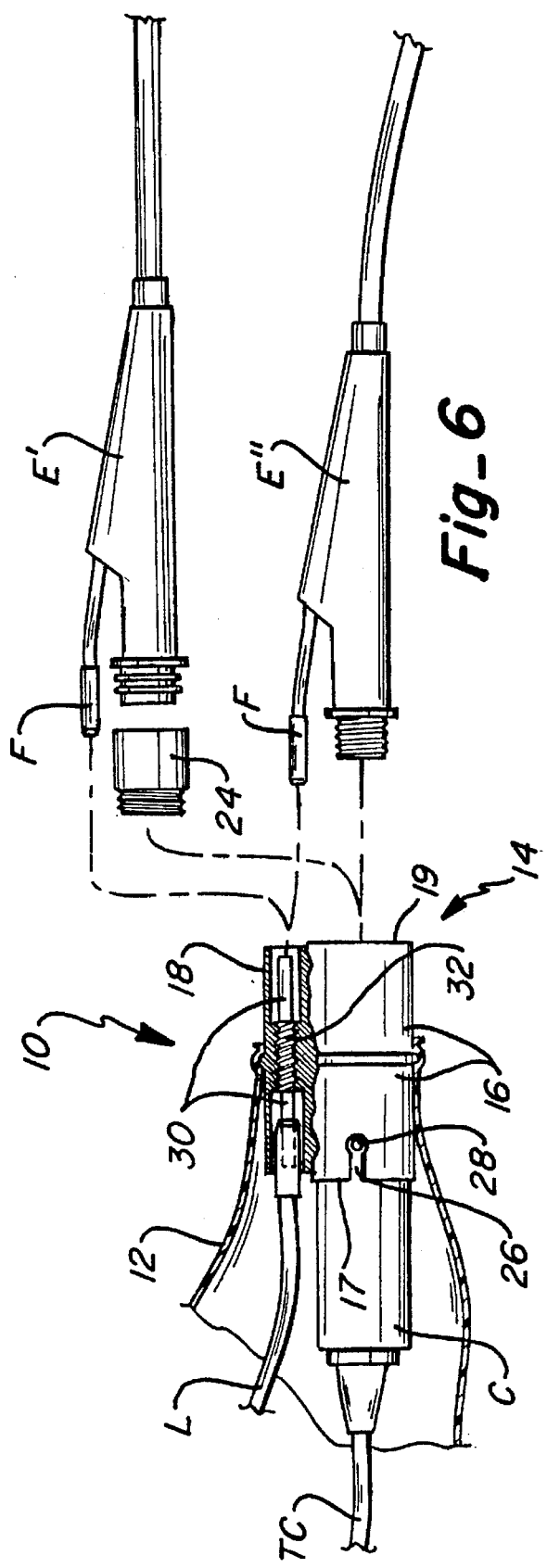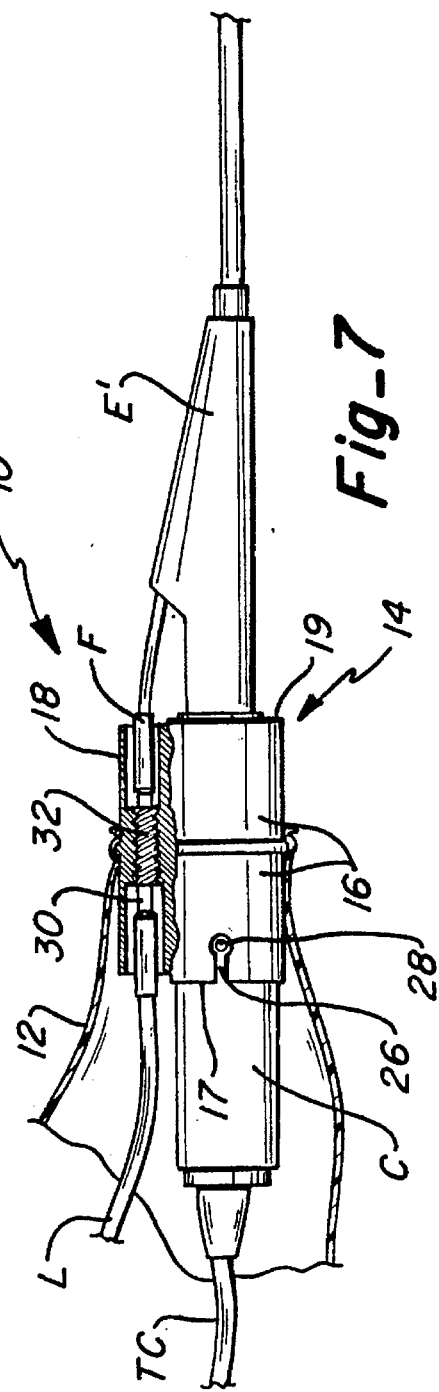

STERILE CONNECTOR AND VIDEO CAMERA COVER FOR STERILE ENDOSCOPE

TECHNICAL FIELD

This invention relates to a sterile connector and video camera cover for use in an operating room environment and more particularly to such a connector and camera cover which encloses and aligns an unsterile camera with a sterile endoscope.

BACKGROUND ART

It is common in the art to find unsterile cameras used in surgery that are enclosed by some type of sterile covering in order that the camera can be coupled to a sterile endoscope or other surgical viewing device. Typically, such coverings include an open distal end or a window providing a clear optical path between the camera and endoscope.

Medical devices such as endoscopes and cameras continue to rapidly evolve in terms of their technology, one overriding goal being to provide for devices which are smaller in size, lighter in weight, simpler in construction, and more easy to manipulate by surgical personnel. One major disadvantage of the prior art is that coverings used to isolate an unsterile camera had to be used in conjunction with proprietary coupling systems for each manufacturer of the surgical camera or endoscope. That is, while one type of covering could be used, hardware associated with the coupling system between the endoscope and camera was expensive and was not easily interchangeable among differing types of cameras and endoscopes. Also, not all coverings were completely compatible with the proprietary coupling hardware making the coverings less reliable and more difficult to use.

Accordingly, there is a need for a device that may be used to couple varying types of endoscopes and cameras, and to simultaneously provide for a sterile covering that will isolate an unsterile camera and its trailing cables.

One of the more recent developments in endoscope technology is the use of a "rod lens" endoscope having lenses that are formed by injection molding. These endoscopes are very small in size and are easily and inexpensively manufactured. U.S. Pat. No. 3,257,902 to Hopkins teaches the use of a conventional rod-lens endoscope that traditionally incorporated lenses that were manufactured by grinding down the lens to the appropriate size. These new injection molded rod lens endoscopes may not have an eyepiece which reduces their size, and the endoscope is prefocused such that the image produced on a CCD sensor of the camera does not require a complex series of lenses in the camera to achieve proper focus.

Thus, it is one primary object of this invention to provide for a device which allows connection of these new rod lens-type endoscopes to numerous surgical camera-types, and simultaneously provide a sterile covering for the camera and its trailing cables.

Examples of prior art include my earlier U.S. Pat. No. RE. 34,002, entitled "Sterilizable Video Camera Cover". This invention discloses a sterile drape which extends over a camera and its trailing cables, and a connecting structure which allows the video camera to be attached to an endoscope by means of an optical connector known as a "C mount" or "V mount".

An example of prior art teaching a surgical drape is U.S. Pat. No. 5,274,500 to Dunn which discloses a surgical cover for a video camera device providing a sealed, sterile encasement of the camera and its associated transmission cables. This device includes a flexible tubular member and a distal end including a lens which allows the camera to be optically coupled with an endoscope.

U.S. Pat. No. 5,078,483 to Herzberg teaches a sterile disposable camera cover made from a tubular piece of film folded onto itself and forming a package including a plurality of folded layers. An end of the camera extends into and through an end portion of the cover so that both ends of the cover are co-located at the same side of a film package which houses the cover prior to use.

U.S. Pat. No. 5,198,894 to Hicks discloses an endoscope having a sleeve-like drape secured in a retracted position at the proximal end of the endoscope. When the endoscope is secured to a camera, the drape is extended to telescope over and envelope the camera such that the resulting outer surface of the drape in its extended position remains sterile. The drape is attached at the proximal end of the endoscope as opposed to being positioned between the camera and the endoscope.

The prior art is adequate for its intended purpose, however, none of the references cited, either alone or in combination, disclose the novel structure set forth below.

DISCLOSURE OF THE INVENTION

An apparatus is provided for enclosing a nonsterile video camera and its trailing cables in a sterile covering, and a connector assembly for coupling the camera and a light source to an endoscope for use in the sterile environment of an operating room. The apparatus includes a generally cylindrical connector having an outer surface and an inner surface with a diameter of a size to snugly receive a camera through a first open end. A transparent barrier window is mounted within the connector which is contacted by the lens of the camera when positioned inside the apparatus. The connector further includes means for securely attaching the camera in a fixed position, and means for attaching an endoscope to the connector at a second end. A sterile cover is attached to the outer surface of the connector which is extendable back over the trailing cable of the camera for a substantial distance. Mounted on the cylindrical connector is a light source connecting means for coupling a light source by means of a light fiber cable associated with the endoscope. A sterile disposable wand is provided to aid in the attachment of the camera to the connector and is removably attached to the second end of the connector prior to connection with an endoscope. Once the camera is attached to the connector, the wand can be removed and the endoscope can be coupled to the second connector end. The second end of the connector is compatible for receiving endoscopes having either threaded or compression fittings.

With the apparatus just described, it is possible to couple common surgical cameras, such as those that do not include integral light transmitting means, with a sterile endoscope. The unique configuration of the light source connecting means independent of the cylindrical connector allows cameras of all types to be used with different types of rod lens or fiber endoscopes. Furthermore, the "plug in" characteristic of the connector ends and light source connecting means allows a quick and easy way to attach an endoscope to a video camera, the disposable wand providing positive support to aid in coupling the camera to the connector.

Additional advantages of this invention will become apparent from the description which follows, taken in conjunction with the accompanying drawings.

BRIEF DESCRIPTIONS OF THE DRAWINGS

FIG. 1 is a perspective view of a sterile connector assembly and video camera cover constructed in accordance with this invention prior to connection of a camera and a light cable;

FIG. 2 is another perspective view, as shown in FIG. 1, illustrating the disposable wand separated from the connector assembly;

FIG. 3 is an enlarged, fragmentary perspective view showing the connector assembly;

FIG. 4 is an exploded view including fragmentary longitudinal section of the connector assembly and an endoscope adapter for coupling the connector assembly to an endoscope having a compression fitting;

FIG. 5 is a fragmentary longitudinal section, similar to FIG. 4, but illustrating the connector assembly coupled to an endoscope having a threaded fitting;

FIG. 6 is an exploded view including a fragmentary longitudinal section, similar to FIGS. 4 and 5, illustrating the connector assembly coupled to either a rod lens endoscope or a fiber endoscope; and FIG. 7 is yet another fragmentary longitudinal section illustrating a rod lens endoscope of FIG. 6 coupled to the connector assembly.

BEST MODE FOR CARRYING OUT THE INVENTION

In accordance with this invention, a sterile connector and video camera cover 10, as shown in FIG. 1, is provided for use with an unsterile camera C to provide a barrier between the camera C and a sterile endoscope E and to isolate the unsterile camera C, trailing cables TC and light fiber cable L from the surgical room environment.

The overall structure of the invention can best be seen by viewing FIGS. 1 and 2. It comprises a sterile cover 12 which is connected to the exterior surface of connector assembly 14, the assembly 14 being the structural connection between a video camera C and an endoscope E.

As shown in FIG. 3, the assembly 14 includes two major structural subcomponents, namely the camera/endoscope coupling 16 and light fiber connection 18. Coupling 16 is cylindrical shaped with an inner wall having a diameter to receive a camera in a first end 17 and an endoscope in a second opposite end 19. The coupling 16 and connection 18 both have a common exterior surface. Connection 18 also is cylindrical in shape and extends parallel with the coupling 16. A transparent window 22 is mounted within the inner wall of coupling 16 and serves as the barrier between camera C and endoscope E.

Sterile disposable wand 20 is provided for support when attaching the camera C to the first end of coupling 16. After engaging camera C with coupling 16, drape 12 is pulled back over camera C trailing cables, TC and light cable L. The disposable wand 20 is then unscrewed and the desired endoscope is attached to the second end of coupling 16. A cover flange or peripheral rib 21 is provided for connecting the cover 12 to the exterior surface of connector assembly 14. Typically, the cover 12 may be attached to rib 21 as by adhesive.

The first end 17 of coupling 16 has a slot 26 for receiving the ball detent 28 located on camera C. Ball detent 28 and slot 26 are provided in order to rigidly fix the camera in place. It is necessary to rigidly fix the camera in order that the image produced by the camera on a viewing screen remains steady and is properly oriented for viewing. Although a slot-ball detent arrangement is shown, other means to fix the camera in place may be used such as a bayonet-type slot and pin or some other type of locking mechanism.

The second end 19 of coupling 16 may be threaded, or may be configured for receiving an endoscope having a compression fitting. Alternatively, the second end 19 of coupling 16 may receive an adapter 24 having a threaded end and a compression fitting on the opposite end, so enabling the second end 19 of coupling 16 to be compatible to receive either an endoscope having a compression fitting or a threaded fitting.

One of the novel structural features of this device is the light fiber connection 18. It is common to encounter manufacturers of cameras and light source with proprietary configurations for connection of the camera and light source to an endoscope. That is, most miniaturized video cameras and light sources can only be connected with endoscopes having the same type of connecting configuration. The light fiber connection 18 overcomes this disadvantage by providing a means to connect a source of light, such as fiber optic cable light L, directly to an endoscope having a separable light fiber connection illustrated as fitting F in FIGS. 4–7. Accordingly, light fiber connection 18 includes an internal connector tube 30 having a first end for attachment to light cable L and a second end for attachment to light guide fitting F of endoscope E. An interior threaded portion 32 allows connector tube 30 to be adjustably positioned so to match the particular configurations of connections between light source L and fitting F of endoscope E. Alternatively, connector tube 30 may have threaded ends or fittings which are compatible with the particular connections found with cable L and fittings F of endoscope E.

The operation of this device can best be described by the following:

A sterile nurse grasps the sterile disposable wand 20 while an unsterile nurse secures the camera C and inserts the ball detent 28 into groove 26 engaging the camera within the coupling 16. The unsterile nurse then pulls the drape 12 over camera C, trailing cables TC and cable L, thus completely enclosing the elements therein. Next, camera C is held in position by a sterile nurse by grasping the exterior surface of the drape while the sterile disposable wand 20 is detached, as by unscrewing, from the second end 19 of coupling 16. An endoscope E is then attached to the second end 19 of coupling 16, either by direct connection or by means of adapter 24, the window 22 providing a sterile barrier between the endoscope E and the camera C.

Any number of differing types of endoscopes having a separable light guide fitting F may be used with the disclosed invention. For example, as shown in FIGS. 6 and 7, a rod lens endoscope E', or a fiber endoscope E" may be used.

The advantages of the foregoing invention are clear. A connector assembly is provided wherein an endoscope may be optically coupled with a camera, and simultaneously, a light fiber connection is provided for coupling a light carrying fiber optical cable to the fiber optic connection of an endoscope in order to illuminate the surgical area. The light fiber connection is made part of the connection between the camera and the endoscope thus eliminating the need to provide another sterile cover for the fiber optic cable and associated hardware. This invention also provides a system which is "universal" for mating differing cameras to endoscopes having separable light fiber connections. That is, the unique "plug in" or "screw in" feature of the connector assembly substantially reduces connection problems with endoscopes and cameras having incompatible coupling systems, the connector assembly being constructed to accept a multitude of such variations. This also eliminates the common problem of a mismatch between the fiber optic connection on the endoscope and the fiber optic originating from the light source.

This invention has been described in detail with reference to a particular embodiment thereof, but it will be understood that various other modifications can be effected within the spirit and scope of this invention.

I claim:

1. An apparatus for enclosing an unsterile, miniature video camera and its trailing cables and a light fiber cable in a sterile cover and for connecting the camera and the light fiber cable to a sterile endoscope having a separable light guide fitting, said apparatus comprising:

a connector assembly for attachment of the camera to the endoscope and for attachment of the light fiber cable to the light guide fitting, said connector assembly including:

a generally cylindrical coupling having a first end for receiving the camera and a second end for receiving the sterile endoscope;

a transparent window positionable between said first and second ends of said coupling for providing a sterile and optically clear barrier between the camera and endoscope;

means for aligning the camera within said first end of said coupling in a fixed position; and light fiber connecting means mounted to said coupling, said connecting means having a first end for receiving the light fiber cable, and a second end for receiving the light guide fitting of the sterile endoscope; and a flexible sterile cover attachable to said connector assembly and extendable over the camera, the trailing camera cables and the light fiber cable.

2. An apparatus, as claimed in claim 1, further including:

means in said first end of said coupling for rigidly stabilizing said camera within said cylindrical housing.

3. An apparatus, as claimed in claim 1, wherein said light fiber connecting means includes:

a connector tube having first and send ends; and a threaded portion positionable between said first and second ends of said connector tube.

4. An apparatus, as claimed in claim 1, further including:

a sterile disposable wand attachable to said second end of said coupling, said wand stabilizing said apparatus when connecting the camera thereto.

5. An apparatus, as claimed in claim 1, further including:

an adaptor removably attachable to said second end of said coupling for interchangeable connection with the sterile endoscope.

6. A system for providing an image of an operating area during a surgical process, said system comprising:

a miniaturized unsterile video camera having a distal end for receiving light from the operating area;

a coupling means having first and second ends, said first end being attachable to said camera;

an endoscope attachable to said second end of said coupling means, said coupling means having an open internal diameter passing therethrough enabling optical communication of said endoscope with said camera, said endoscope having a separable light guide fitting in communication with light transmitting fibers disposed within said endoscope;

a light fiber connecting means on said coupling means, said light fiber connecting means having first and second ends, and providing a connection between a light fiber cable and said light transmitting fibers of said endoscope; and a transverse window positionable between said camera and said endoscope within said coupling means, said window providing a transparent and sterile barrier between said endoscope and said camera.

7. An apparatus, as claimed in claim 6, wherein said light fiber connecting means includes:

a connector tube having first and second ends; and a threaded portion positionable between the ends of said connector tube.

8. An apparatus, as claimed in claim 7, further including: a sterile disposable wand attachable to said second end of said connector for providing support to said apparatus when connecting the camera thereto.

9. An apparatus, as claimed in claim 7, further including: an adaptor removably attachable to said second end of said coupling for interchangeable connection with said sterile endoscope.

10. A method of connecting an unsterile camera to a sterile endoscope in an operating room and isolating the unsterile camera and its unsterile trailing cables from the sterile environment within the operating room, said method comprising the steps of:

providing a sterile coupling having a telescoping sterile cover and having a first end for receiving an unsterile camera and a second end for receiving a sterile endoscope and having a window forming a clear optical path and a barrier between the first and second ends;

supporting the coupling with a sterile wand attached to the second end of the coupling;

attaching the camera to the first end of the coupling;

pulling the sterile cover over the unsterile camera and trailing ends;

detaching the wand from the second end of the coupling; and attaching the sterile endoscope to the second end of the coupling.

11. A method of connecting an unsterile surgical camera and an unsterile light providing fiber optic cable to a sterile endoscope having a separable light guide fitting, and isolating the unsterile camera, its unsterile trailing cables, and the unsterile light providing fiber optic cable from the sterile environment within an operating room, said method comprising the steps of:

providing a sterile coupling having a telescoping sterile cover and having a first end for receiving the unsterile camera and a second end for receiving the sterile endoscope and having a window forming a clear optical path and a barrier between the first and second ends;

providing a sterile light fiber connecting means integral with the sterile coupling, the connecting means having a first end for receiving the fiber optic cable and a second end for receiving the light guide fitting of the endoscope;

supporting the coupling and connecting means with a sterile wand attached to the second end of the coupling;

attaching the camera to the first end of the coupling;

attaching the fiber optic cable to the first end of the connecting means;

pulling the sterile cover over the unsterile camera, its trailing cables, and the fiber optic cable;

detaching the wand from the second end of the coupling; and attaching the sterile endoscope to the second end of the coupling and the light guide fitting of the endoscope to the second end of the connecting means.

* * * * *

UNITED STATES PATENT AND TRADEMARK OFFICE
CERTIFICATE OF CORRECTION

PATENT NO. : 5,498,230
DATED : Mar. 12, 1996
INVENTOR(S) : Edwin L. Adair

It is certified that error appears in the above-indentified patent and that said Letters Patent is hereby corrected as shown below:

Item [56],
On the cover page, after "U.S. Patent Documents" insert
```
--4,914,521   4/1990    Adair
--5,078,483   1/1992    Herzberg
--RE 34,002   7/1992    Adair
--5,198,894   3/1993    Hicks
--5,237,984   8/1993    Williams, III, et al.
--5,274,500   12/1993   Dunn
--5,325,846   7/1994    Szabo
```

Signed and Sealed this

Fifth Day of October, 1999

Attest:

Q. TODD DICKINSON

Attesting Officer

*Acting Commissioner of Patents and Trademarks*